(12) United States Patent
Kitamura et al.

(10) Patent No.: US 7,364,430 B2
(45) Date of Patent: Apr. 29, 2008

(54) DENTAL IMPLANT SYSTEM AND METHOD

(76) Inventors: Akira Kitamura, 36-26, Shiroyamadai 2-Chome, Nagasaki-shi, Nagasaki 852-8027 (JP); Ryoji Kitamura, 36-26, Shiroyamadai 2-Chome, Nagasaki-shi, Nagasaki 852-8027 (JP)

(*) Notice: Subject to any disclaimer, the term of this patent is extended or adjusted under 35 U.S.C. 154(b) by 0 days.

(21) Appl. No.: 11/437,191

(22) Filed: May 18, 2006

(65) Prior Publication Data

US 2006/0204929 A1    Sep. 14, 2006

Related U.S. Application Data

(63) Continuation of application No. 10/956,559, filed on Oct. 1, 2004, now Pat. No. 7,125,253, which is a continuation-in-part of application No. PCT/JP03/03903, filed on Mar. 27, 2003.

(30) Foreign Application Priority Data

Apr. 4, 2002   (JP) .............................. 2002-102295

(51) Int. Cl.
 *A61C 8/00*   (2006.01)
(52) U.S. Cl. ................... 433/173; 433/167; 433/215
(58) Field of Classification Search ................ 433/173, 433/172, 215, 167; 128/898
See application file for complete search history.

(56) References Cited

U.S. PATENT DOCUMENTS

| | | | | |
|---|---|---|---|---|
| 1,216,683 A | * | 2/1917 | Greenfield | 433/165 |
| 3,592,554 A | * | 7/1971 | Takahara | 408/204 |
| 4,787,848 A | * | 11/1988 | Ross | 433/165 |
| 4,820,156 A | * | 4/1989 | Ross | 433/165 |
| 5,118,294 A | * | 6/1992 | Kurer | 433/220 |
| 5,397,235 A | * | 3/1995 | Elia | 433/173 |
| 5,711,315 A | * | 1/1998 | Jerusalmy | 128/898 |
| 5,961,329 A | * | 10/1999 | Stucki-McCormick | 433/173 |
| 5,989,025 A | * | 11/1999 | Conley | 433/76 |
| 6,916,322 B2 | * | 7/2005 | Jesch | 606/80 |
| 6,923,650 B2 | * | 8/2005 | Kurer | 433/220 |
| 2002/0177102 A1 | * | 11/2002 | Martin et al. | 433/173 |

* cited by examiner

*Primary Examiner*—Melba N. Bumgarner
*Assistant Examiner*—Jonathan Werner
(74) *Attorney, Agent, or Firm*—Alleman Hall McCoy Russell & Tuttle LLP

(57) ABSTRACT

A dental implant system and method are provided. The dental implant system typically includes a boring device for boring a hole in an alveolar bone and leaving a bridge portion separating the hole from the maxillary sinus cavity. The system may also include a scoring device for scoring the bridge portion, and a lifting device for breaking the bridge portion along the score, and lifting the freed bridge portion a first predetermined distance. The system may further include a membrane separation elevator for separating the sinus membrane from the sinus cavity wall. The system may also include a second lifting device configured to contact the freed bridge portion to further raise the freed bridge portion and sinus membrane together to a second predetermined penetration distance into the sinus cavity.

10 Claims, 16 Drawing Sheets
(3 of 16 Drawing Sheet(s) Filed in Color)

DENTAL IMPLANT SYSTEM AND METHOD

CROSS-REFERENCE TO RELATED APPLICATIONS

This application is a continuation of U.S. application Ser. No. 10/956,559, filed Oct. 1, 2004 now U.S. Pat. No. 7,125,253, entitled DENTAL IMPLANT SYSTEM AND METHOD, which in turn is a continuation-in-part of PCT International Application No. PCT JP03/03903, now published as WO 03/084426, filed Mar. 27, 2003, entitled DRILL DEVICE FOR IMPLANTING, which in turn claims priority to Japanese Patent Application No. 2002-102295, filed Apr. 4, 2002. The entire disclosure of each of these applications is herein incorporated by reference for all purposes.

TECHNICAL FIELD

The present invention generally relates to an implant system including a plurality of dental devices and an implant method for using same to install a dental implant in an alveolar bone of a maxilla of a patient.

BACKGROUND

One type of dental implant typically is cylindrical in shape with an outer diameter of between about 4 and 5 millimeters, and is inserted to a fixed depth into the alveolar bone of the maxilla (upper jaw). For patients with an alveolar bone thickness of more than about 5 millimeters, this type of implant may be secured in a relatively stable manner. However, for patients with less than 5 millimeter alveolar bone thickness, dental surgeons use a procedure known as sinus lift bone augmentation to build up the thickness of the alveolar bone of the maxilla, so that dental implants may be securely installed therein.

As shown in FIG. 1, prior sinus lift bone augmentation procedure requires that the side wall bone of the maxillary sinus cavity be broken and a hole opened therein. The sinus cavity membrane is separated from the upper surface of the maxilla, and an elevator material made of a mixture of bone material and blood serum is inserted through the hole in the side of the maxilla and placed at the bottom of the sinus cavity between the maxilla and the sinus lining. The elevator material hardens over time to increase the effective thickness of the maxilla, thereby providing additional stability for the implant.

While this prior sinus lift bone augmentation procedure may be effective when performed by highly skilled surgeons, it nonetheless involves several inherent risks. First, exposure of the bone when the side wall of the sinus cavity is broken creates the risk of infection. Second, breaking the bone in the side wall or bottom of the sinus cavity creates a risk of penetration of the membrane lining the sinus cavity, which can further result in infection. Finally, during installation of the elevator material and implant itself, it is difficult to judge the amount of elevator material and depth of implant penetration into the sinus cavity, creating a risk that insufficient filler has been added, which could weaken the implant, or a risk of overpenetration by the elevator material or implant, which could damage the sinus membrane. If the sinus membrane is ruptured, the transplanted elevator material may become infected. Further, this complicated procedure may involve hospitalization of the patient, which is time consuming and expensive.

It is also known to punch through from a tooth socket into the maxillary sinus cavity using a circular instrument as illustrated in FIG. 2. The instrument is then removed to form a hole in which an implant may be fastened. However, when using this procedure, it is difficult to determine whether the lower portion of the maxillary sinus cavity can be safely lifted up without fracture of the alveolar bone and the bottom of the sinus cavity wall. Therefore, success of this procedure is greatly dependent upon the skill of the dental surgeon performing the operation.

SUMMARY

A dental implant system and method are provided. The dental implant method typically includes forming a hole in bone of an alveolar of a maxilla, adjacent a sinus cavity. The hole is initially formed so as to leave a bridge portion separating the hole from a bottom surface of a sinus cavity wall. The method may further include freeing the bridge portion from the sinus cavity wall, and lifting the bridge portion and the sinus membrane together at least partially into the sinus cavity.

According to another aspect of the invention, the method may further include separating the sinus membrane from the sinus cavity wall, to thereby create a void, and further lifting the freed bridge portion into the sinus cavity to enlarge the void. The method may further include placing elevator material into the void, and inserting an implant into the hole, such that an inward end of the implant extends into the void and is surrounded by elevator material.

The dental implant system typically includes a scoring device having a shaft sized to be inserted into a predrilled hole in the alveolar bone. A bridge portion is formed in the alveolar bone at an end of the hole which separates the hole from the maxillary sinus cavity. The scoring device typically further includes a scoring edge positioned adjacent a distal end of the shaft, the scoring edge being configured to form a circular score in a portion of the alveolar bone when the shaft is rotated and pressed into the alveolar bone. The scoring device typically further includes a cavity formed inside of the scoring edge, the cavity being sized to accommodate bone material as the scoring edge penetrates the alveolar bone.

The implant system may further include a first lifting device having a shaft sized to be inserted into the hole. The first lifting device further typically includes a lifting portion positioned adjacent a distal end of the shaft, the lifting portion being sized to contact the bridge portion inward of the score, such that when upward pressure is applied to the lifting portion, the lifting portion is configured to break the alveolar bone along the score to free the bridge portion.

The implant system may further include a membrane separation elevator having a separation elevator shaft, and a separation elevator head that is substantially flat and attached at a distal end of the shaft. The separation elevator shaft is configured to be inserted through the neck in the hole, into the sinus cavity. The separation elevator head is configured to be inserted between a sinus membrane and the sinus cavity wall, to cause separation therebetween.

The implant system may further include a second lifting device having a second lifting device shaft sized to be inserted into the hole, and a second lifting device end portion positioned adjacent a distal end of the shaft. The second lifting device end portion is typically longer than the first lifting device end portion and has a diameter that is sized to fit into the neck of the hole. The second lifting device end portion is configured to contact the freed bridge portion to further raise the freed bridge portion and sinus membrane together to a second predetermined penetration distance into the sinus cavity.

BRIEF DESCRIPTION OF THE DRAWINGS

The patent or application file contains at least one drawing executed in color. Copies of this patent application publication publication with color drawing(s) will be provided by the Office upon request and payment of the necessary fee.

DETAILED DESCRIPTION OF THE EMBODIMENTS

Figure 1:
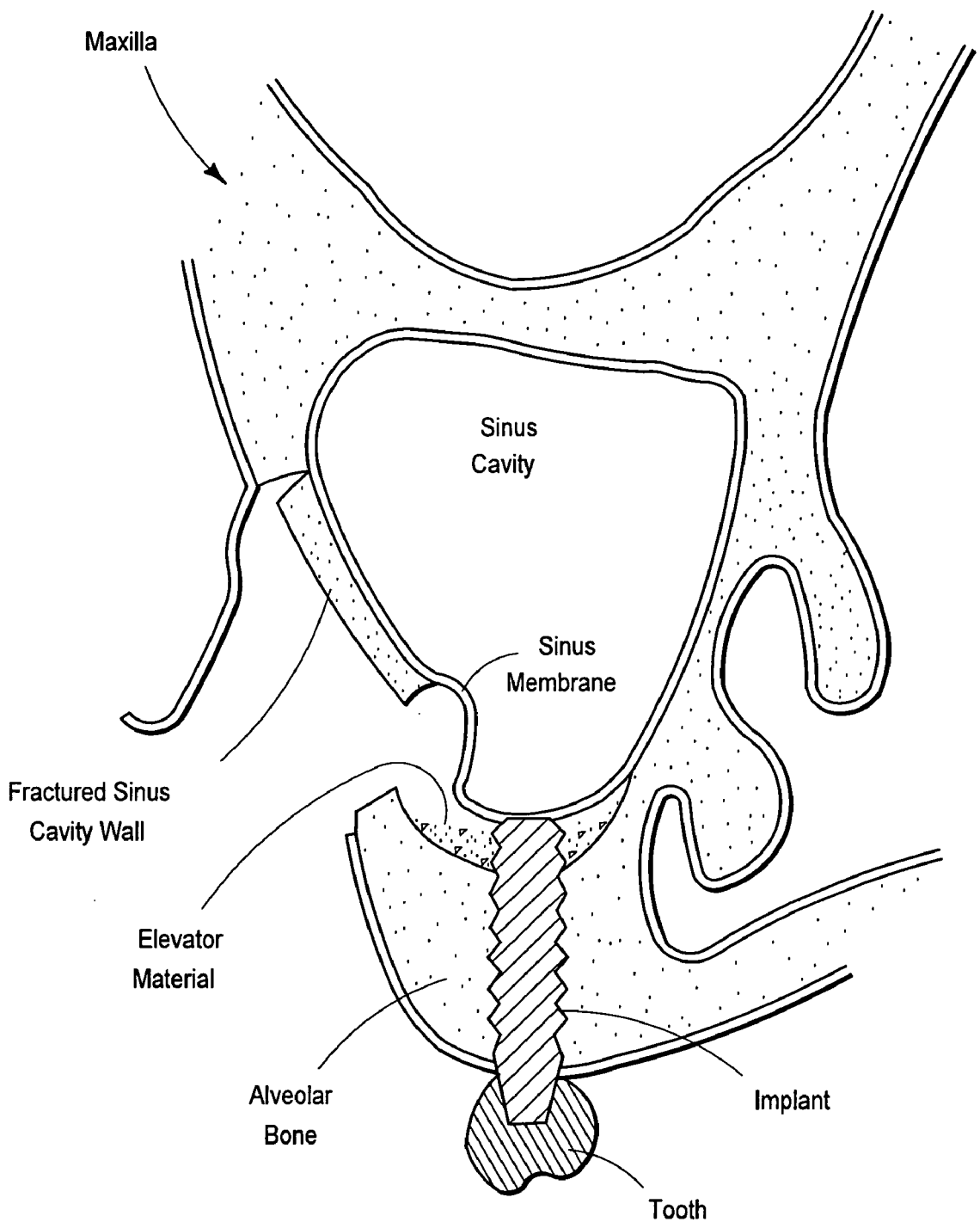
FIG. 1 is a cross-sectional view of a dental implant installed according to a prior art sinus lift bone augmentation procedure.
Figure 2:
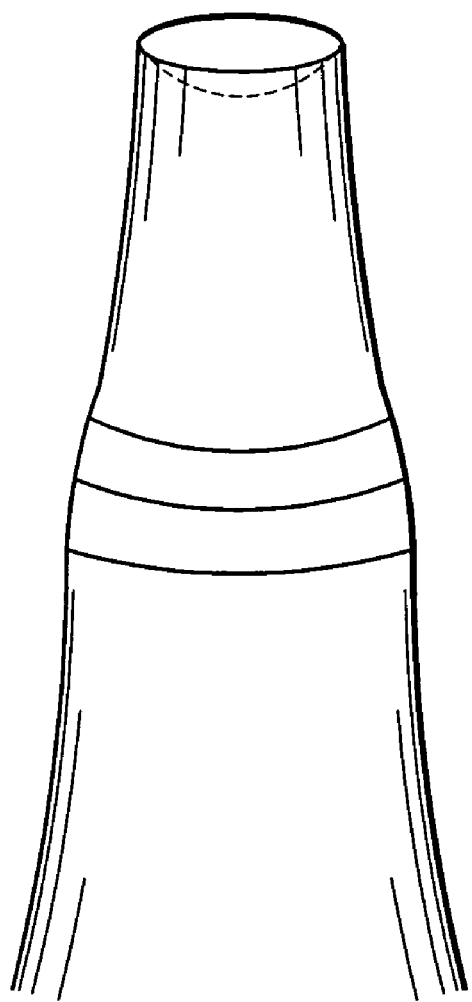
FIG. 2 is frontal view a prior art circular instrument for punching a hole in an alveolar bone to install a dental implant.
Figure 3:
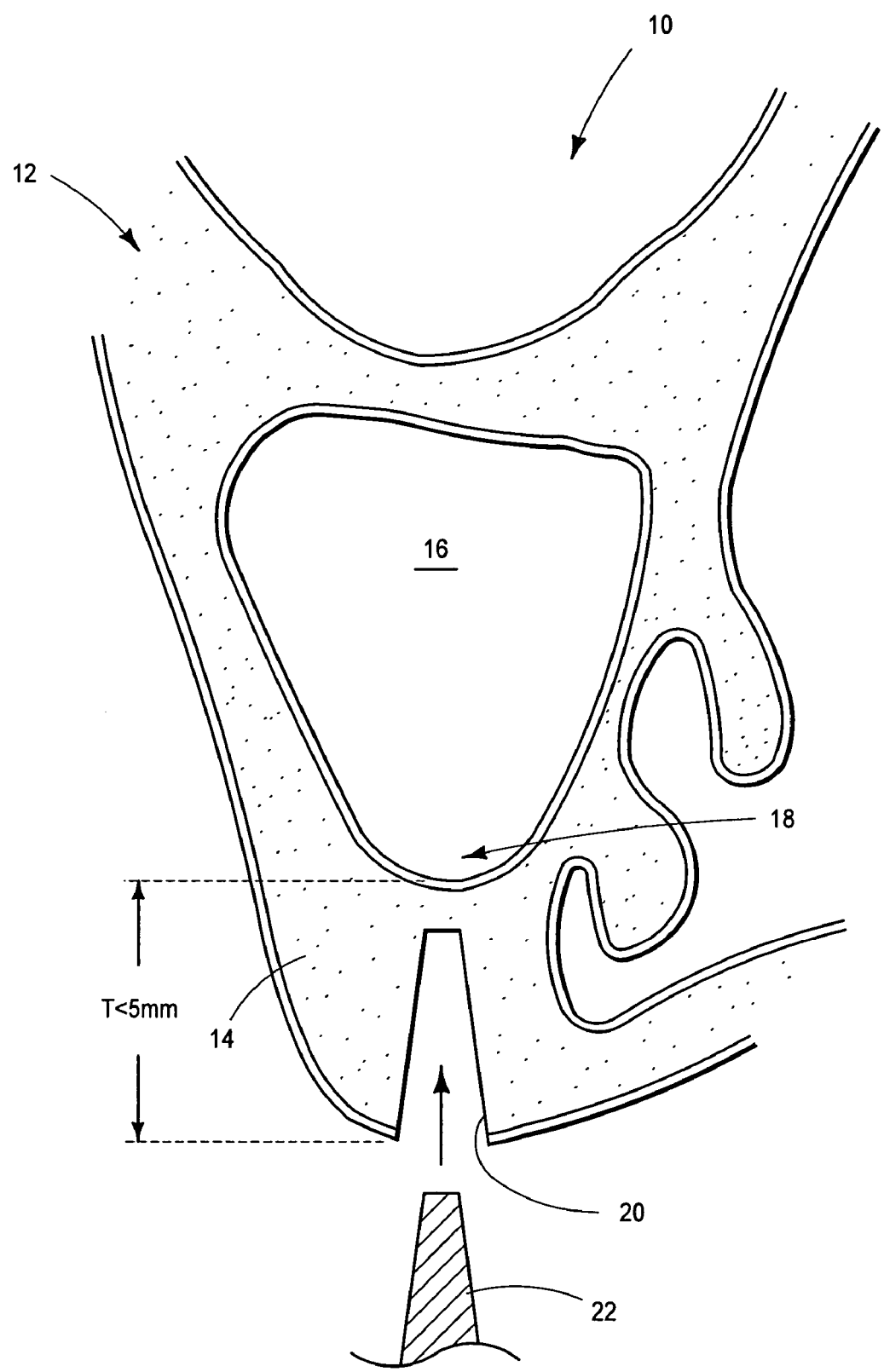
FIG. 3 is a cross-sectional view of an alveolar bone and maxillary sinus cavity, illustrating a predrill device used to predrill a hole according to one embodiment of a method for implanting a dental implant according to the present invention.

FIGS. 3-9 illustrate a method of implanting a dental implant, according to one embodiment of the present invention. FIG. 3 illustrates a cross section of a patient upper jaw region 10, showing a maxilla 12 having an alveolar bone 14 with a thickness T of less than about 5 millimeters (drawing not to scale) between the bottom of a sinus cavity 16 and a lower surface of the alveolar bone 14. This thickness is typically insufficient to properly support a dental implant, and therefore a sinus lift bone augmentation method according to the present invention may be used to add bone material in a lower region 18 of the sinus cavity 16 to provide additional support to the implant.

The implant method typically includes predrilling a hole 20 in alveolar bone 14 of the maxillary 12 with a predrill device 22. Typically, predrill device 22 is a tapered drill with a base diameter of approximately 3 millimeters. Alternatively, drills of other suitable sizes and shapes may be used. The predrill hole is formed to stop short of sinus cavity 16, and is formed with tapered sides, in a frustoconical shape.

Figure 4:
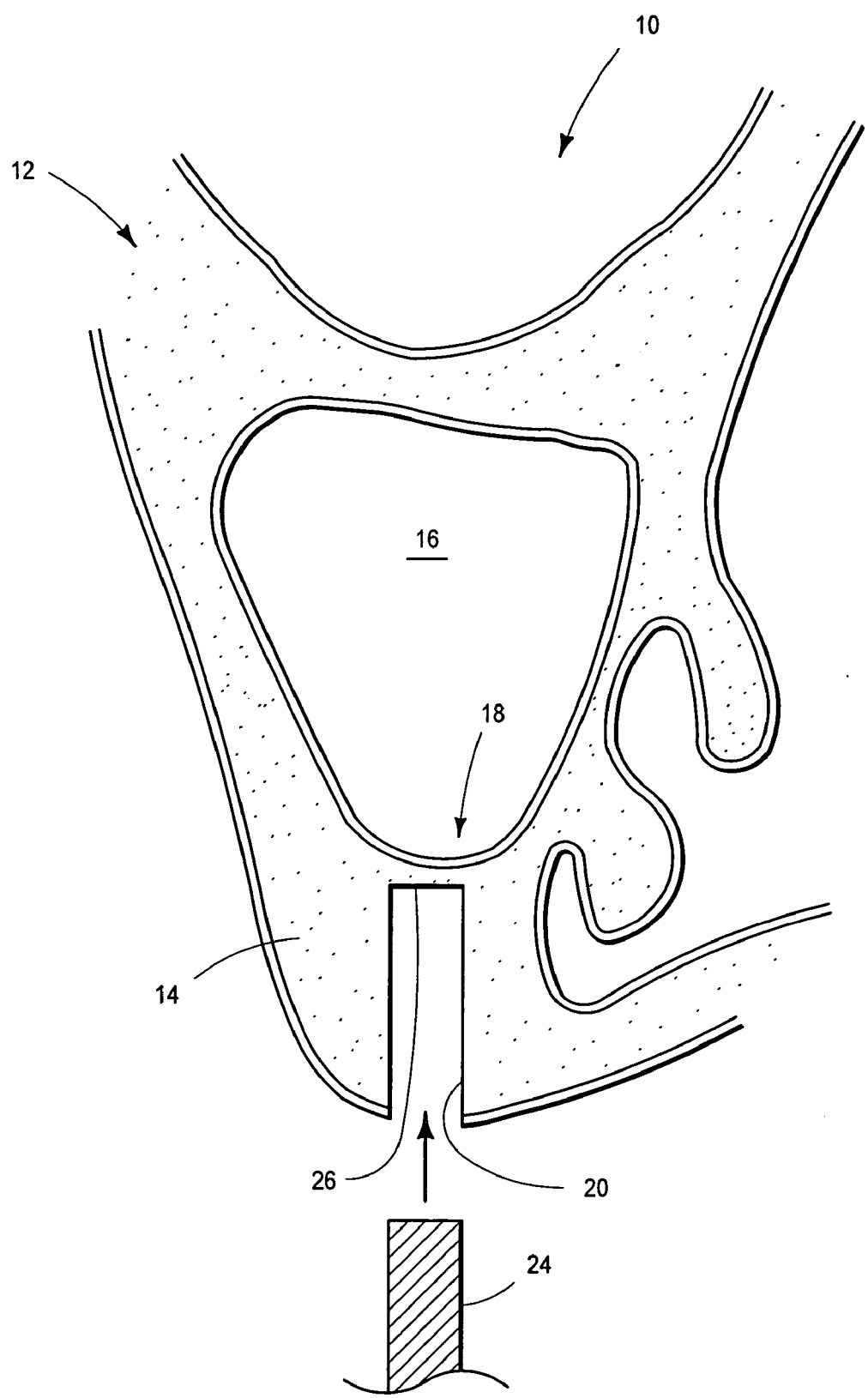
FIG. 4 is a cross-sectional view of an alveolar bone and maxillary sinus cavity, illustrating a boring device used in boring a hole in the alveolar bone.

As shown in FIG. 4, the implant method further typically includes boring a hole using a boring device 24 to remove the taper formed by the predrill device, and to leave a narrow bridge portion 26 remaining between the hole 20 and a lower region 18 of the sinus cavity 16. Typically, the bridge portion 26 is formed to a thickness of between 0.5 and 2 millimeters, and more typically to about 1 millimeter. The thickness of the bridge portion is ascertained by referencing tomography images of the patient jaw structure, and by visually monitoring a depth gauge formed by markings or grooves (see 70-76 in FIG. 10 or 130 in FIG. 13) on the boring device 24 as the device is inserted and twisted to deepen and bore out hole 20. It will be appreciated that the various other devices described herein are similarly marked to provide a depth gauge. Boring device 24 is typically connected to a handle, and is rotated by hand at low speed to prevent the generation of heat that might damage the bone.

Figure 5:
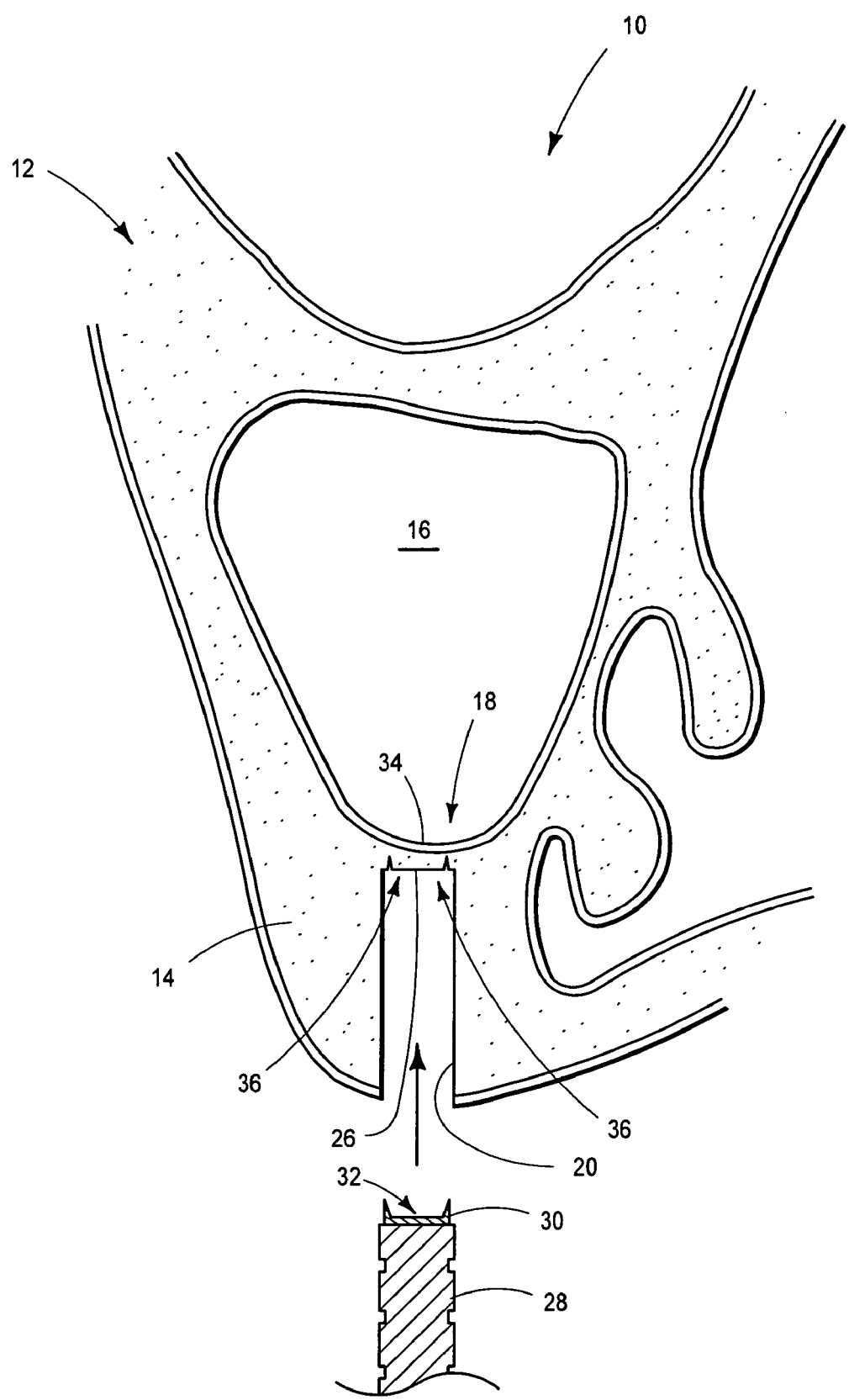
FIG. 5 is a cross-sectional view of an alveolar bone and maxillary sinus cavity, illustrating a scoring device used in scoring a bridge portion formed in the alveolar bone.

As shown in FIG. 5, the method typically includes scoring a bottom side of the bridge portion 26 with a scoring device 28. The scoring device is typically rotated by hand. The scoring device includes a scoring structure 30 configured to score the alveolar bone at the top end of hole 20. Typically, the scoring structure is a sharp, raised scoring edge formed in a circle around a circumference of a top portion of the scoring device. Alternatively, a blade that does not extend around the entire circumference may be used. A concavity 32 is formed within the scoring structure, to accommodate bone material as the scoring device is pressed into the bone surface. The cavity of the scoring device includes a floor configured to contact a portion of the alveolar bone to thereby stop penetration of the scoring edge into the alveolar bone at a predetermined penetration distance. The score 36 typically extends substantially all of the way through bridge portion 26, but does not extend all of the way through.

The scoring device is twisted by hand and forced into the bone by applying pressure sufficient to score the bone. Care is taken not to rotate bridge portion 26 relative to sinus membrane 34, which could damage the sinus membrane 34 and potentially cause infection. A narrow score 36, or indentation 36, is formed by rotation of the scoring device into bridge portion 26. Typically the scoring tool includes a lip or edge, as shown at 81 in FIG. 11 and 136 in FIG. 14, and the scoring edge is configured to form the circular score 36 inward of the edges of hole 20, such that the score 36 has a diameter that is less than the outside diameter of hole 20.

Figure 6:
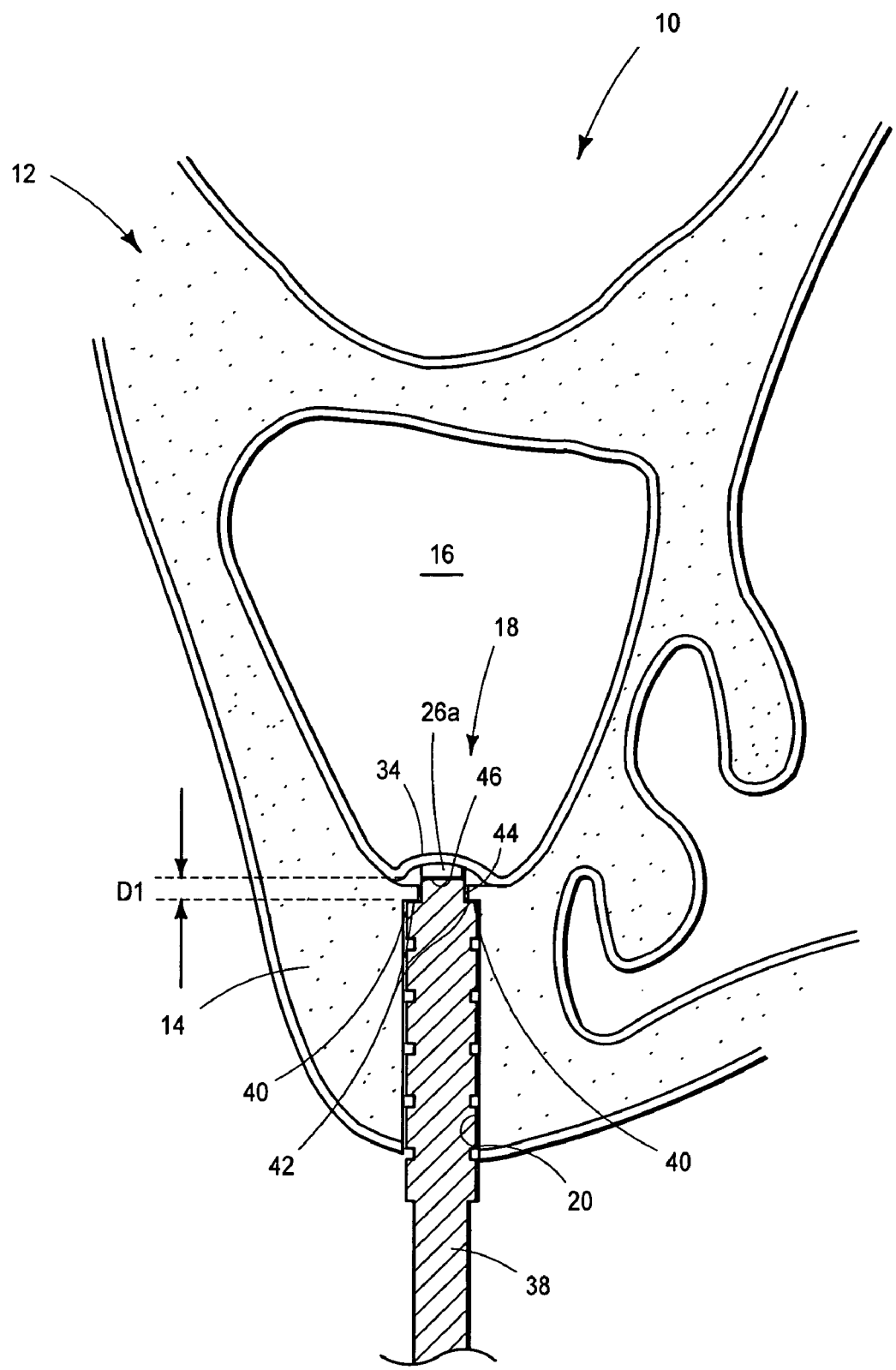
FIG. 6 is a cross-sectional view of an alveolar bone and maxillary sinus cavity, illustrating a first lifting device used in lifting a bridge portion and sinus membrane at least partially into the maxillary sinus cavity.

As shown in FIG. 6, the method includes lifting a portion of the sinus membrane 34 in tandem with the bridge portion 26, by inserting a first lifting device 38 into hole 20 and applying upward pressure. The bone breaks along the score 36 to thereby free the bridge portion, and create a freed bridge portion 26a. Because score 36 is formed inward of the sides of hole 20, as the freed bridge portion is raised, overhang portions 40 are formed along the sides of the hole, creating a narrowed neck at the upper end of the hole between the overhang portion 40. Typically, care is taken not to rotate the first lifting device 38 during the lifting operation, which could cause the bridge portion to rotate relative to the membrane. This prevents undesirable shear or tearing of the membrane.

The first lifting device is typically pushed upward a first predetermined lift distance D1 into the sinus cavity. Typically, the first lifting device includes a lip 42 configured to contact the overhang portions 40 of hole 20, when the freed bridge portion 26a reaches the first predetermined lift distance D1. A lifting portion 44 of the first lifting device 38 is formed such that a top surface 46 of the lifting portion supports the bridge portion 26a at the first predetermined lift distance D1 when the overhang portions 40 contact lip 42. This contact prevents further ingress of the first lifting device 38. In addition, markings that function as a depth gauge are provided on the shaft (see 152 in FIG. 15A and 102-108 in 12A), which may be visually monitored by the dental surgeon performing the operation to judge lift distance. It will be appreciated that according to another embodiment of the invention, overhang portions 40 may be omitted, and the dental surgeon performing the procedure may rely only on markings or grooves along the devices themselves to determine penetration distance, rather than on contact between a lip of a tool and an overhang portion of hole 20.

The predetermined lift distance D1 is a distance effective to allow the membrane separating device access to the sinus cavity, but not so far as to cause damage to sinus membrane 34. The first predetermined lift distance D1 typically is between 0.5 and 1.5 millimeters, and more typically is 1 millimeter, although variations are possible.

Figure 7:
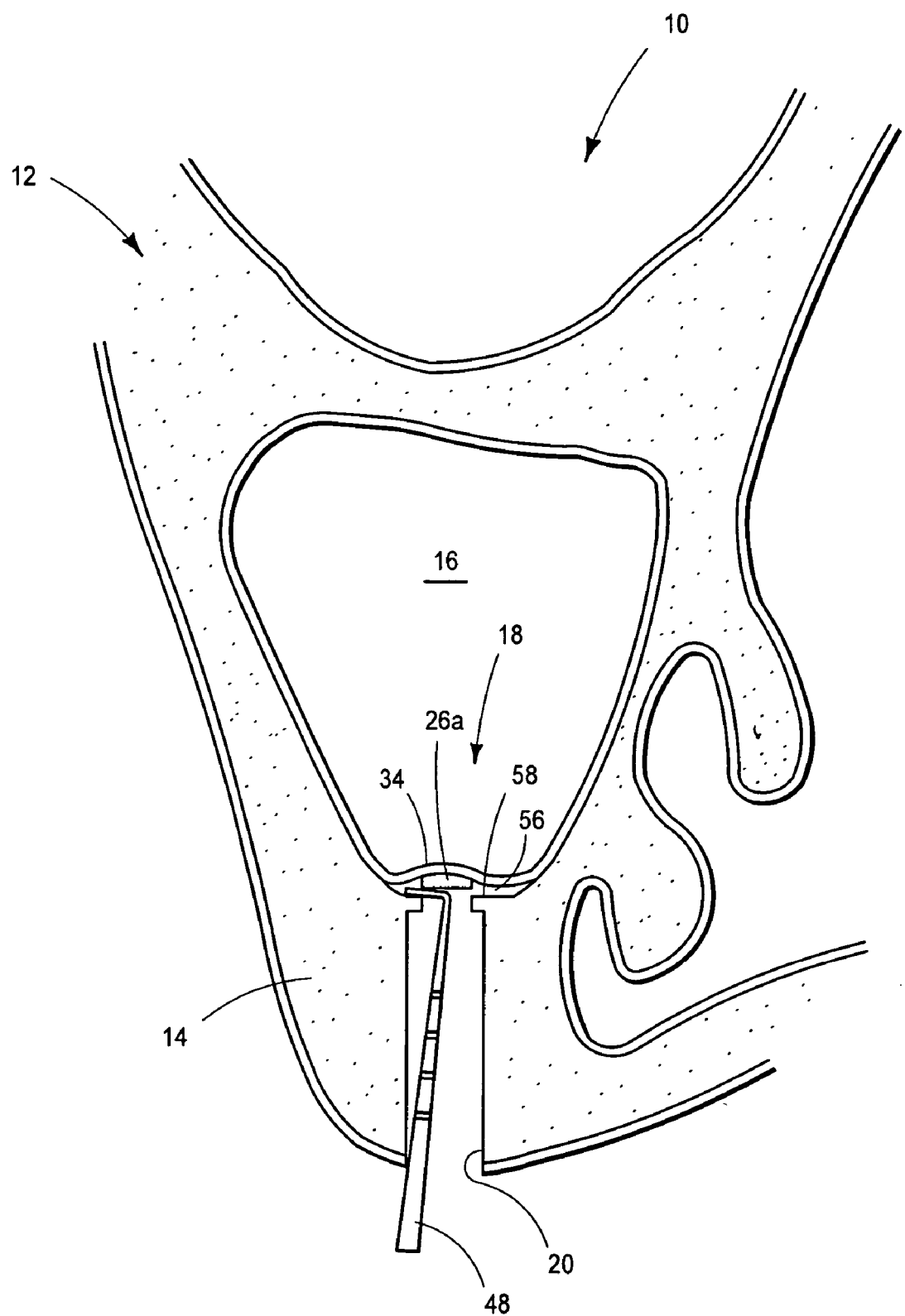
FIG. 7 is a cross-sectional view of an alveolar bone and maxillary sinus cavity, illustrating a membrane separating device used to separate the sinus membrane from a sinus cavity wall.
Figure 16A:
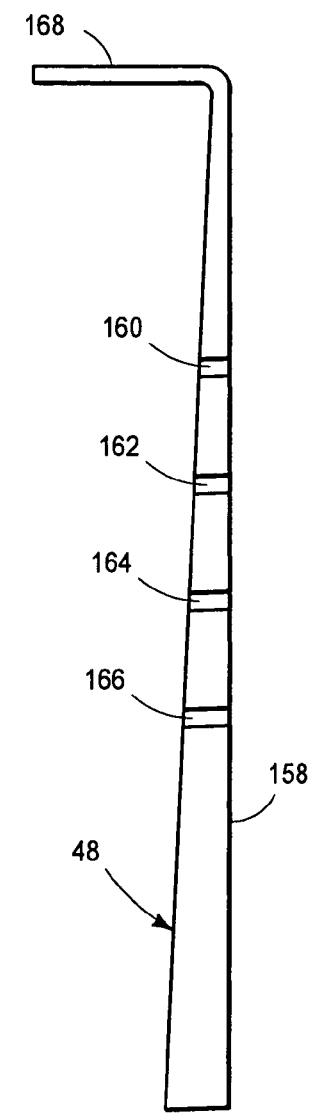
FIG. 16A is a front perspective view of a membrane separation elevator according to an embodiment of the present invention.
Figure 16B:
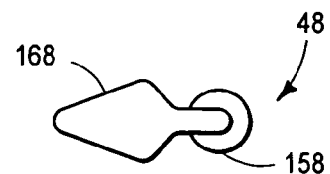
FIG. 16B is a top view of the membrane separation elevator of FIG. 16A.

As shown in FIG. 7, the method includes separating the sinus membrane 34 from a sinus cavity wall 58 using a membrane separation elevator 48. As shown in FIG. 16B, membrane separation elevator 48 typically includes a flat, substantially triangular head 168. Head 168 is inserted between the sinus membrane 34 and the sinus cavity wall 58, and is rotated around the circumference of the upper opening of hole 20, to separate the membrane from the sinus cavity wall 58. As shown in FIG. 16A, membrane separation elevator 48 also typically includes grooves or markings 160-166, which form a depth gauge that indicates a penetration depth into the hole 20.

Figure 8:
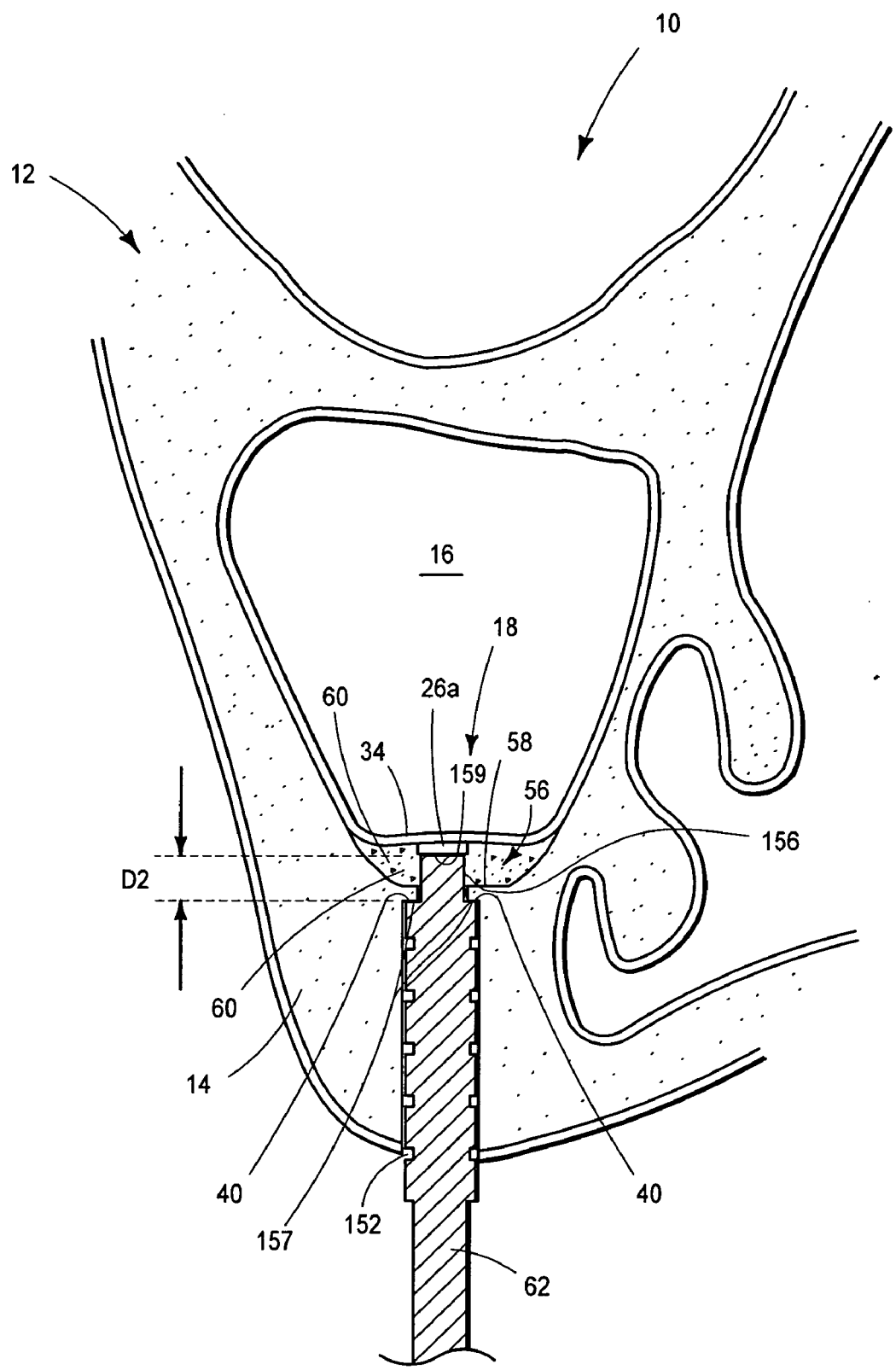
FIG. 8 is a cross-sectional view of an alveolar bone and maxillary sinus cavity, illustrating a second lifting device used to further lift a bridge portion and sinus membrane into the maxillary sinus cavity.

As shown in FIG. 8, the method may further include lifting the freed bridge portion 26a a second predetermined lift distance D2, using a second lifting device 62 having a lifting portion 156 with an effective length (length from top surface 159 to lip 157) that is greater than the first lifting device 38. Typically, the dental surgeon performing the implant method references grooves 152 or markings to judge penetration depth into hole 20. In the act of lifting the freed bridge portion 26a to the second predetermined lift distance D2, the sinus membrane 34 is further separated from the sinus wall 58. The second predetermined lift distance D2 is typically between 2 and 4 millimeters, and is more typically 3 millimeters. As shown in detail in FIG. 15B, the second lift device typically lifting portion 156 typically has a reduced outer diameter relative the diameter of shaft 154, with a lip 157 formed therebetween. The top surface 159 is placed against the bottom of the freed bridge portion 26a and the freed bridge portion is pushed to the second predetermined lift distance D2, at which point contact between lip 157 and overhang portions 40 prevents further ingress of the second lift device 62. Lifting of the bridge portion 26a and membrane forms a lift region 56 in the gap between the bottom surfaces thereof and the upper surface of the sinus cavity wall 58.

The second lifting device 62 subsequently may be removed, and an elevator material 60 of bone powder and blood plasma may packed into the lift region 56 below lifted sinus membrane 34 and sinus cavity wall 58. Typically the elevator material is made from bone and blood serum obtained from the patient when opening hole 20. The volume of elevator material is typically calculated by making reference to a computer tomography scan of the sinus cavity, and performing volumetric calculations to estimate the size of lift region 56, less the volume to be taken by the implant itself. Alternatively, other suitable method may be used to estimate the amount of elevator material.

Figure 9:
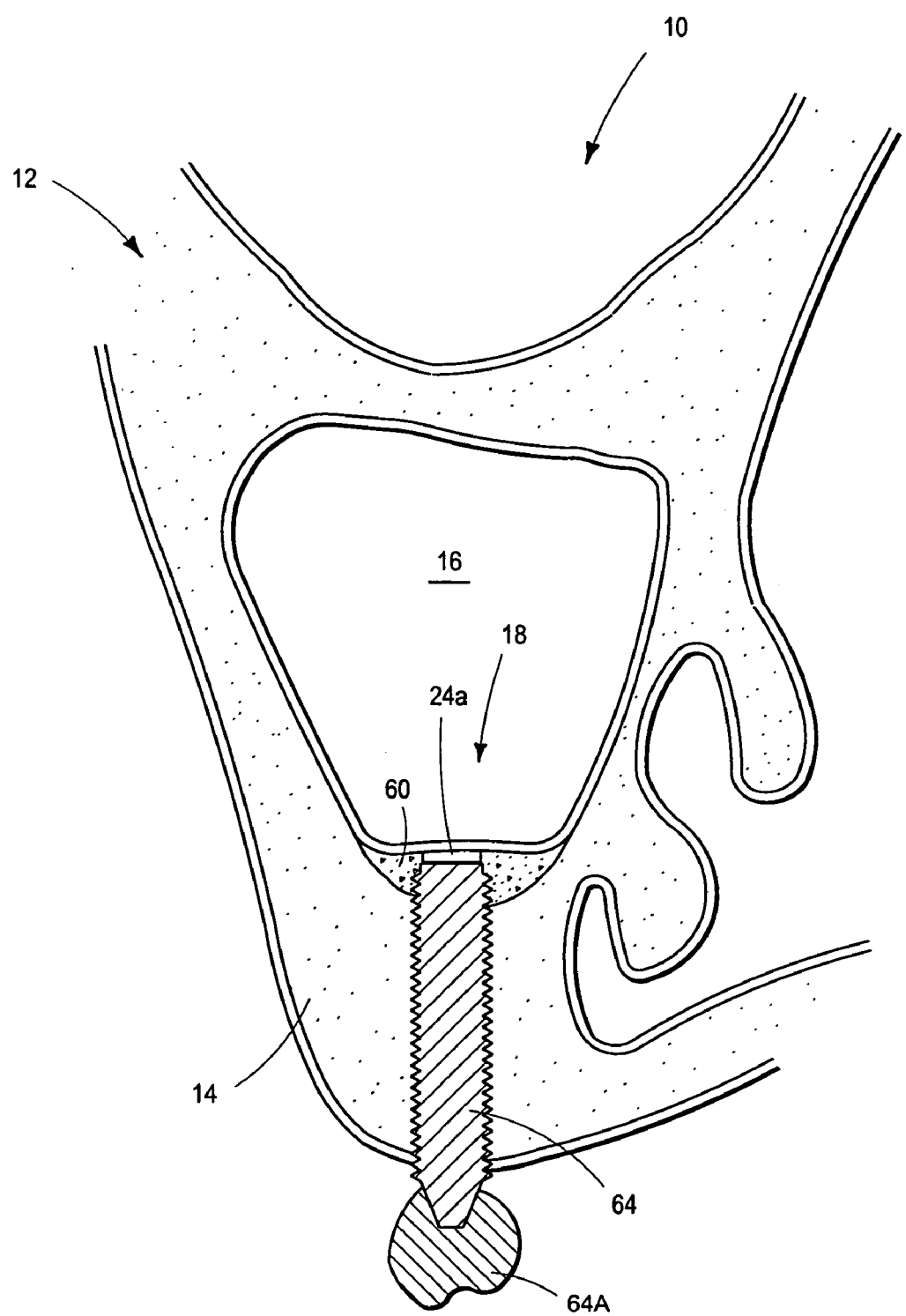
FIG. 9 is a cross-sectional view of an alveolar bone and maxillary sinus cavity, illustrating a dental implant installed according to the implant method illustrated in FIGS. 3-8.

As shown in FIG. 9, after the lift region is packed with elevator material 60, an implant 64 is typically inserted and an artificial tooth 64a is secured to an end thereof. Typically, the diameter of the implant is slightly larger than the hole 20, to form an effective interference fit when inserted. For example, the hole may be formed to approximately 3 millimeters in diameter, and the implant may have a diameter of 4 millimeters, with an abrasive surface having depressions to a depth of approximately 0.3 millimeters from the outer diameter of the implant 64.

Figure 10:
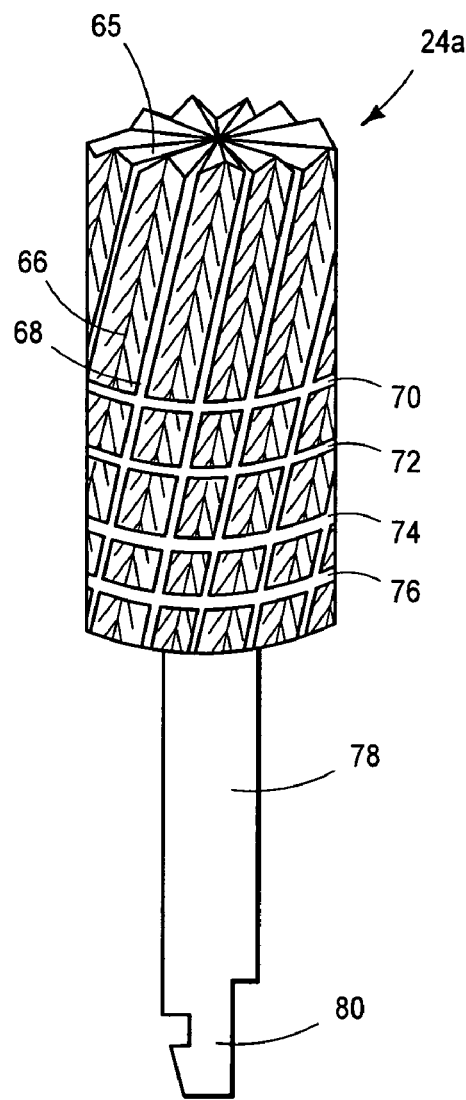
FIG. 10 is a front perspective view of a boring device according to one embodiment of the present invention.

FIGS. 10-16 illustrate a set of devices forming an implant system for performing the above-described implant method. FIG. 10 is a detail view of one embodiment of a boring device 24a according to the present invention. Boring device 24a typically includes a shaft having a top cutting surface 65, a side cutting surface 66, with longitudinal grooves 68 formed at an angle along the side cutting surface 66. Longitudinal grooves 68 are configured to allow flow of blood and bone material along the sides of the boring device 24a. Lateral grooves 70-76 serve as markings forming a depth gauge that may be used by a dental surgeon to judge penetration depth of the boring device. The grooves may be calibrated at virtually any suitable distance. For example, groove 70 may formed 4 millimeters from the top cutting surface 65, groove 72 may be formed 6 millimeters from the top cutting surface, groove 74 may be formed 8 millimeters from the top cutting surface, and groove 76 may be formed 10 millimeters from the top cutting surface. A shank 78 with a clip 80 is provided for mounting to a handle for hand rotation, or alternatively to a machine for mechanically driven rotation.

Figure 11:
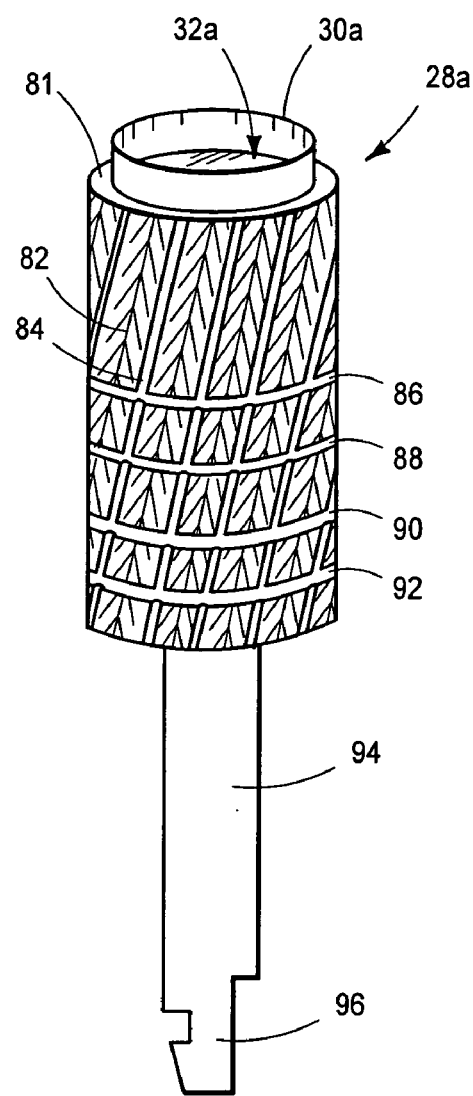
FIG. 11 is a front perspective view of a scoring device according to one embodiment of the present invention.

FIG. 11 illustrates one embodiment of a scoring device 28a according to one embodiment of the present invention. As described above, scoring device 28a typically includes a scoring structure extending upward from a top structure of a shaft of the scoring device. The scoring structure is typically a raised scoring edge extending around the circumference of a cavity 32a. The scoring structure 30a is typically circular and has an outer diameter less than an outer diameter of the shaft of the scoring device, such that a lip 81 is formed intermediate the scoring structure and shaft. Scoring device 28a further includes an exterior cutting surface 82, longitudinal grooves 84, a depth gauge formed by lateral grooves 86-92, a shank 94, and a clip 96. These features are similar to those found in boring device 24a, and will not be redescribed in detail.

Figure 12A:
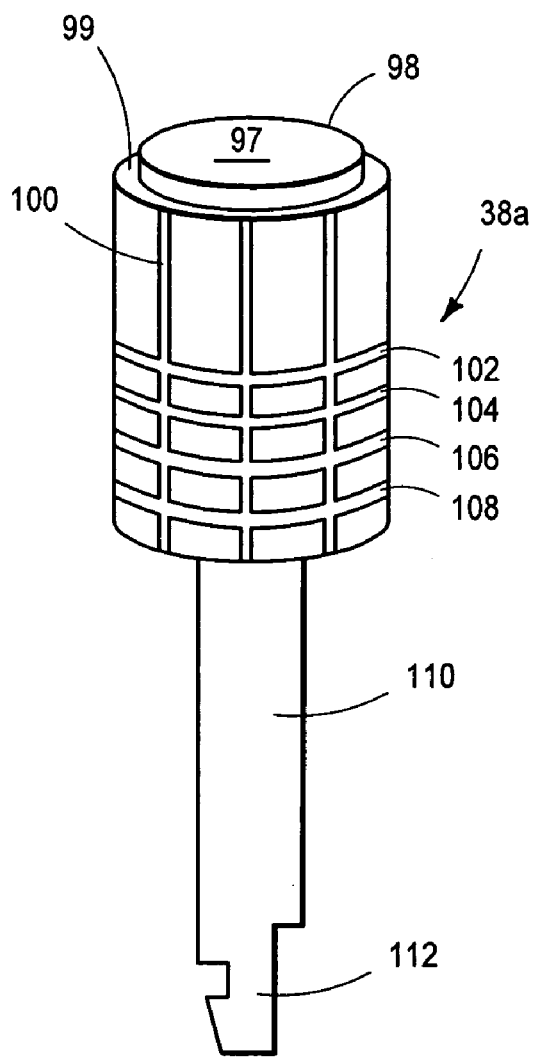
FIG. 12A is a front perspective view of a first lifting device according to one embodiment of the present invention.

FIG. 12A illustrates one embodiment of a first lifting device 38a. First lifting device 38a typically includes a flat top surface 97 positioned on a lifting portion 98. Typically, a lip 99 is formed by a reduction in diameter from a shaft of the first lifting device to the lifting portion 98. The shaft of the first lifting device typically includes longitudinal grooves 100 and lateral grooves 102-108, which form a depth gauge similar to that found on the boring device and scoring device described above. First lifting device 38a further typically includes a shank 110 and clip 112, which may be configured to be attached to a handle or mechanical driver.

Figure 12C:
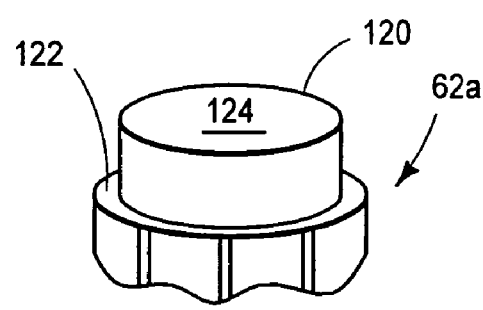
FIG. 12C is a partial front perspective view of a second lifting device according to another embodiment of the present invention.
Figure 12B:
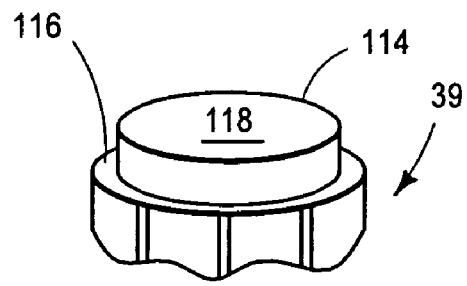
FIG. 12B is a partial front perspective view of an intermediate lifting device according to another embodiment of the present invention.

It will be appreciated that lifting portions of various sizes may be provided on the end of a lifting device of the type shown at 38a. FIG. 12B illustrates an intermediate lifting device 39 with a lifting portion 114 having an intermediate height, as measured between lip 116 and a top surface 118. FIG. 12C shows a second lifting device 62a having lifting portion 120 with a greater height, as measured between lip 122 and top surface 124. According to one embodiment, the height of lifting portion 98 is 1 millimeter, the height of lifting portion 114 is 2 millimeters, and the height of lifting portion 120 is 3 millimeters. While FIGS. 6 and 8 illustrate use of the first and second lifting devices 38, 62, it will be appreciated that an additional intermediate lifting step may be performed using the intermediate lifting device 39, in between the steps illustrated in FIGS. 6 and 8.

Figure 13:
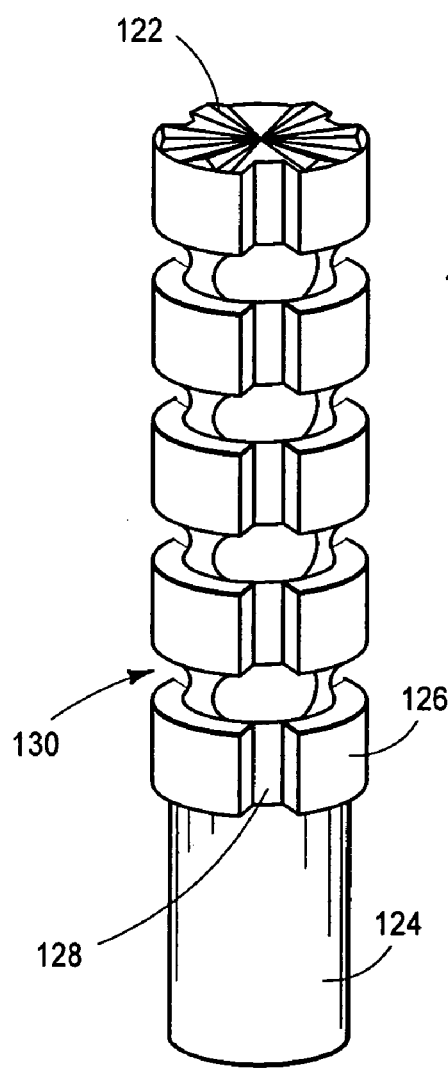
FIG. 13 is a front perspective view of a boring device according to another embodiment of the present invention.

FIG. 13 illustrates a boring device 24 according to another embodiment of the present invention. Boring device 24 includes a top cutting surface 122 positioned at a top of shaft 124. The boring device further includes a plurality of lateral cutting elements 126, which are separated from each other by longitudinal grooves 128, and lateral grooves 130. Typically the boring device and scoring device are of a similar length and width. It will therefore be appreciated that FIGS. 13 and 14 are not to scale.

Figure 14:
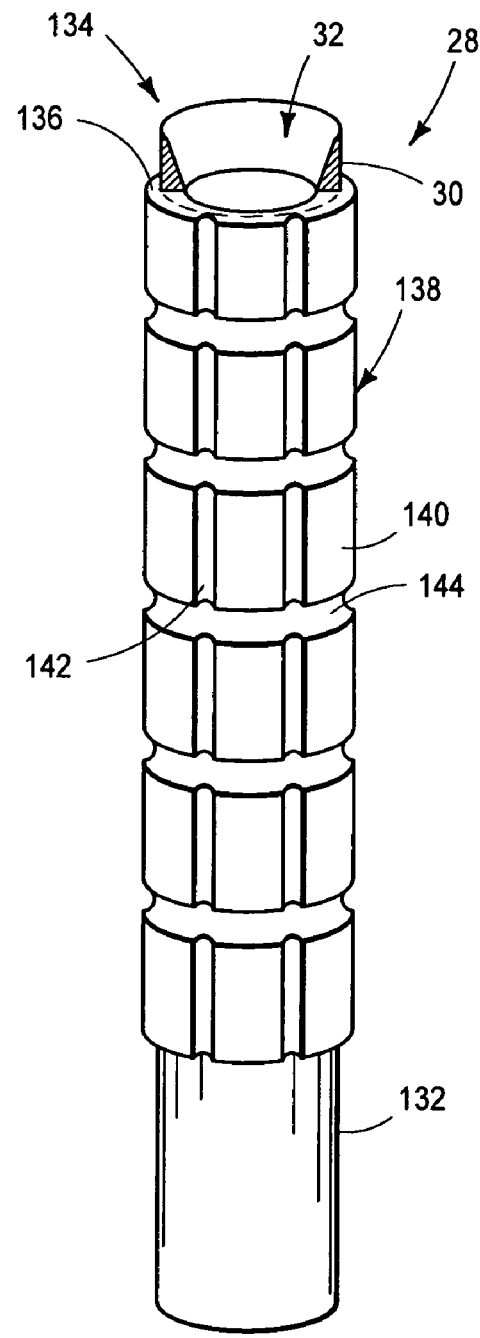
FIG. 14 is a front perspective view of a scoring device according to another embodiment of the present invention.

FIG. 14 illustrates a scoring device 28 according to another embodiment of the present invention. As described in part above, scoring device 28 typically includes a shaft 132 having a raised scoring structure 30 formed at a top end 134 thereof. Raised scoring structure 30 is typically formed around a circumference of cavity 32, which is sized to accommodate bone material when cutting score 36 in bridge portion 26, as described above. The scoring structure 30 is typically circular, and has a diameter that is less than an outer diameter of shaft 132. A lip 136 is formed intermediate scoring structure 30 and shaft 132. Circular bands 138 of raised portions 140 are formed along shaft 132. Raised portions 140 are separated from one another by longitudinal grooves 142, which serve as a depth gauge as described above, and lateral grooves 144, which accommodate the passage of fluid and crushed bone along the length of the shaft.

Figure 15A:
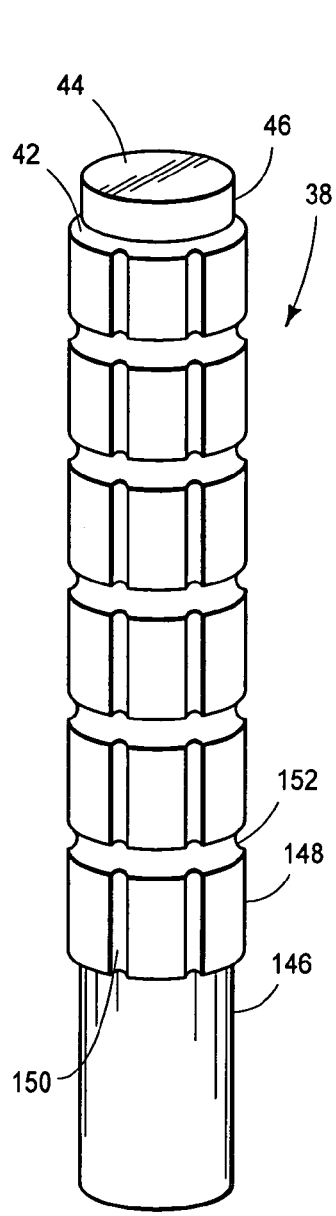
FIG. 15A is a front perspective view of a first lifting device according to another embodiment of the present invention.

FIG. 15A illustrates another embodiment of a first lifting device 38 according to the present invention. First lifting device 38 typically includes a shaft 146 with a lifting portion 46 formed at the top thereof, and a lip 42 formed therebetween. A top surface 44 of the lifting portion is typically flat and spaced apart from lip 42. The height of the lifting portion 46 is sized so that when inserted into the hole 20, the bridge portion 26 is raised to the first predetermined lift distance D1, as shown in FIG. 6. The outer diameter of the lifting portion 46 is typically less than the outer diameter of shaft 146. Shaft 146 further includes a plurality of raised portions 148 separated by longitudinal grooves 150 and lateral grooves 152, similar to scoring device 28.

Figure 15B:
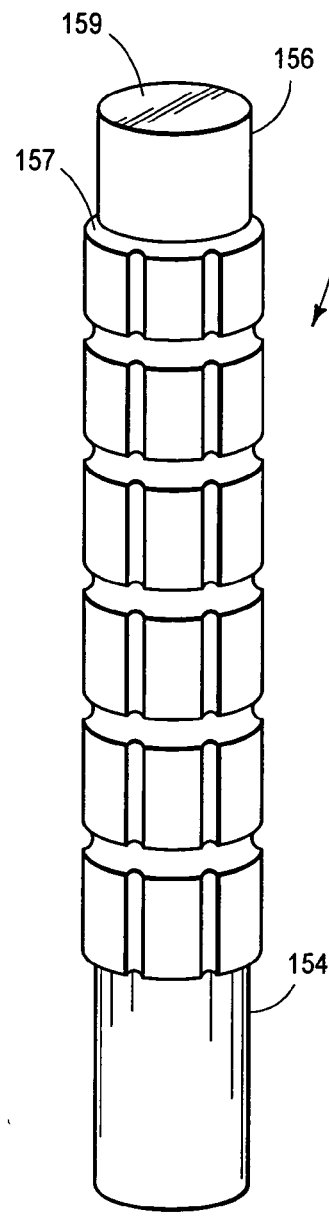
FIG. 15B is a front perspective view of a second lifting device according to another embodiment of the present invention.

FIG. 15B illustrates another embodiment of a second lifting device 62, having a shaft 154 and lifting portion 156 positioned at a top end thereof. Lip 157 is positioned intermediate the shaft and lifting portion. A flat top surface 159 is typically provided at a height relative to lip 157 sized such that the lifting portion raises the bridge portion to the second predetermined lift distance D2, when inserted into hole 20 as shown in FIG. 8.

FIG. 16A illustrates a membrane separation elevator 48 having a shaft 158, with indicia or grooves 160-166 positioned along a length thereof to provide a depth gauge. As shown in FIG. 16B, membrane separation elevator 48 includes a substantially flat, generally triangular head, formed with large diameter radiuses, so as to minimize sharp corners that may damage sinus membrane 34. It will be appreciated that other suitable shapes may be used for head 168, such as circular or oval shapes.

Figure 17:
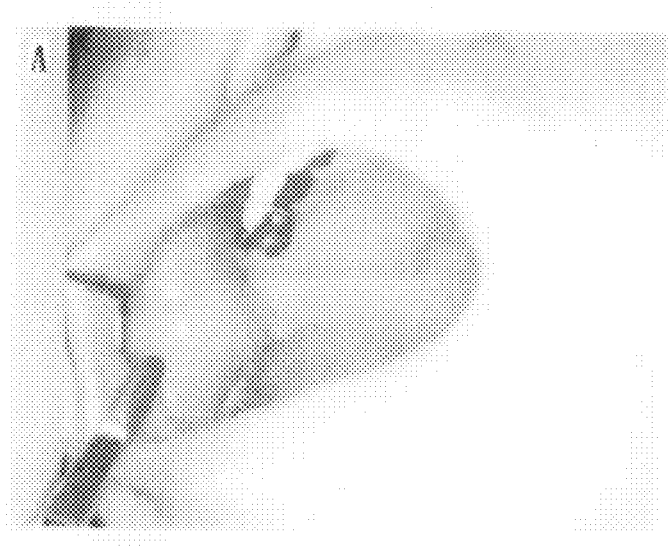
FIG. 17 is a pre-operative intra-oral photograph of a dental implant patient.
Figure 18:
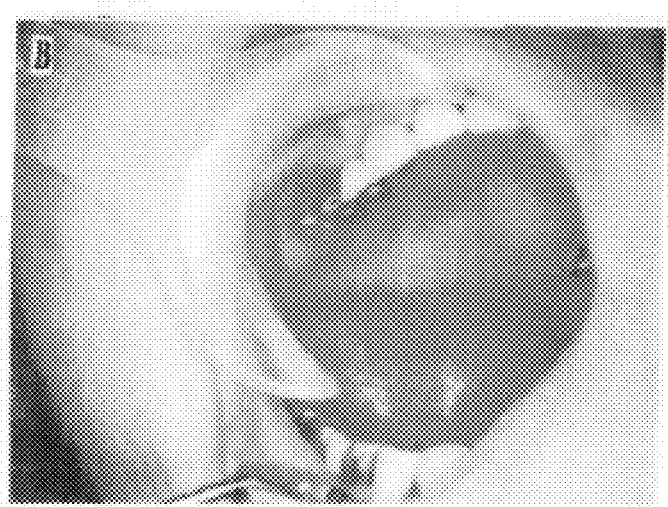
FIG. 18 is a post-operative intra-oral photograph of the patient of FIG. 17, showing an installed implant.

FIGS. 17 and 18 are pre-operative and post-operative intra-oral photographs of a patient on whom the above-described devices and methods were used to install a dental implant.

Figure 19:
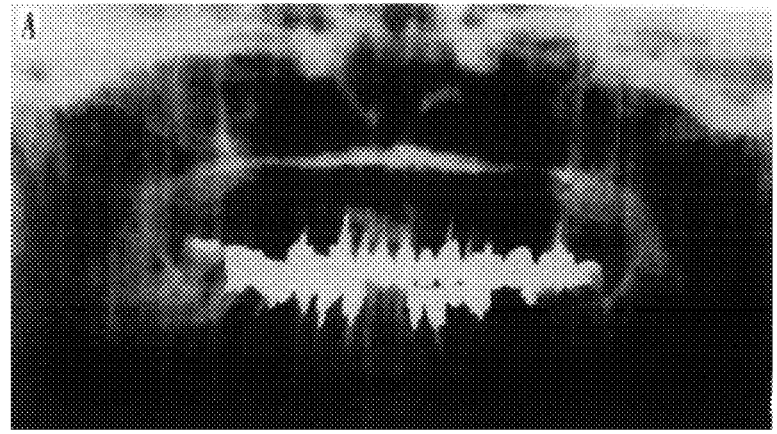
FIG. 19 is a pre-operative panoramic tomography of the patient of FIG. 17.
Figure 20:
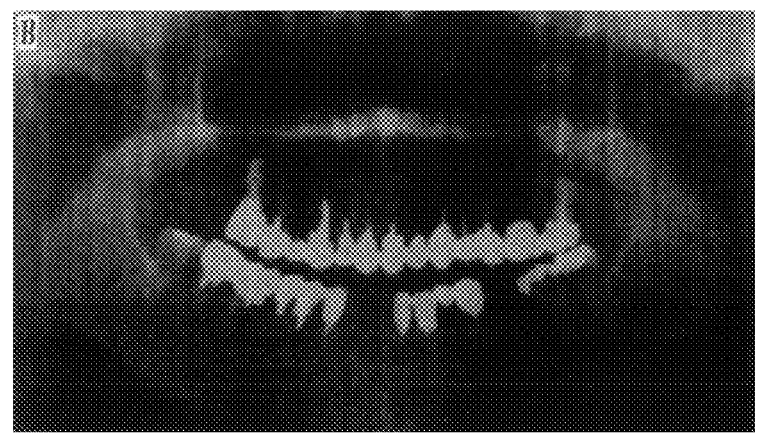
FIG. 20 is a post-operative panoramic tomography of the patient of FIG. 17, showing an installed implant.

FIGS. 19 and 20 are pre-operative and post-operative panoramic tomographies of the patient of FIGS. 17 and 18.

Figure 21:
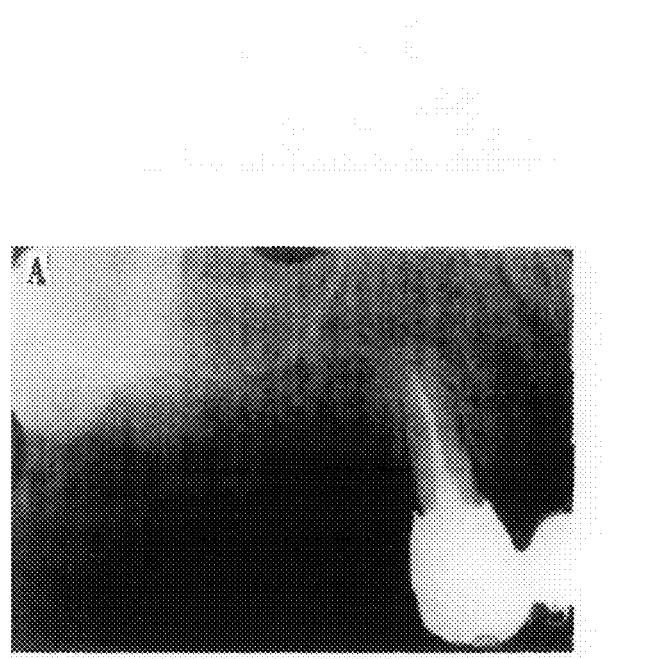
FIG. 21 is a pre-operative inter-oral radiography of an implant region of the patient of FIG. 17.
Figure 22:
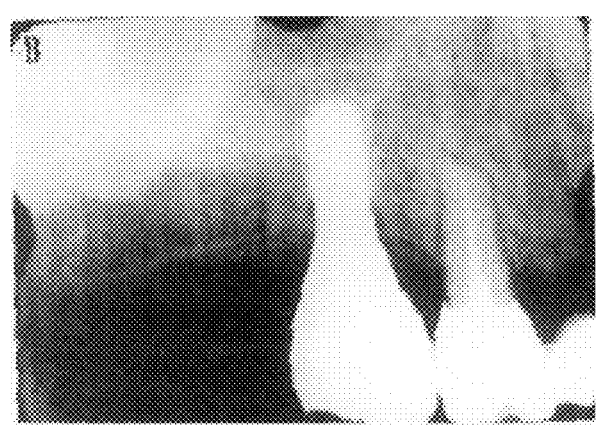
FIG. 22 is a post-operative inter-oral radiography of an implant region of the patient of FIG. 17, showing an installed implant.

FIGS. 21 and 22 are pre-operative and post-operative inter-oral radiographies of an implant region of the patient of FIGS. 17 and 18.

Although the present invention has been shown and described with reference to the foregoing operational principles and preferred embodiments, it will be apparent to those skilled in the art that various changes in form and detail may be made without departing from the spirit and scope of the invention. The present invention is intended to embrace all such alternatives, modifications and variances that fall within the scope of the appended claims.

The invention claimed is:

1. A dental implant system for use in installing a dental implant in a hole in an alveolar bone of a maxilla, adjacent a sinus cavity having a sinus membrane lining the sinus cavity, the hole being formed with a bridge portion separating the hole from a bottom surface of a sinus cavity wall, the dental implant system comprising:

a scoring device including a circular shaft with a circular scoring structure formed at a top end of the shaft, the scoring structure including a raised scoring edge formed around a circumference of a concavity formed within the scoring structure, wherein the scoring structure has an outer diameter that is less than an outer diameter of the shaft, and wherein the scoring device further includes a radially outwardly extending step-shaped lip formed intermediate the scoring structure and the shaft, and wherein the scoring structure is configured to cut a score for use in separating the bridge portion from the sinus cavity wall to form an overhang portion along a side of the hole, adjacent an upper opening of the hole;

a first lifting device including a circular shaft, a circular lifting portion of a first height positioned adjacent a top end of the shaft, and a radially outwardly extending lip formed intermediate the shaft and the lifting portion, wherein an outer diameter of the shaft of the first lifting device is substantially the same as the outer diameter of the shaft of the scoring device, and an outer diameter of the lifting portion is substantially the same as the outer diameter of the scoring structure of the scoring device, and wherein the lip of the first lifting device is complimentarily step-shaped to the lip of the scoring device and to the overhang portion, such that the first lifting device is configured to be inserted into the hole until the lip contacts the overhang portion, to thereby position the bridge portion at a first predetermined lift distance into the sinus cavity.

2. The dental implant system of claim 1, further comprising a membrane separation elevator configured to be inserted between a sinus membrane and the sinus cavity wall, to cause separation therebetween.

3. The dental implant system of claim 1, further comprising a second lifting device including a circular shaft, a circular lifting portion of a second height that is greater than the first height, the circular lifting device further including a radially outwardly extending lip formed intermediate the shaft and the lifting portion, wherein an outer diameter of the shaft of the second lifting device is substantially the same as the outer diameter of the shaft of the scoring device, and an outer diameter of the lifting portion of the second lifting device is substantially the same as the outer diameter of the scoring structure of the scoring device, and wherein the lip of the second lifting device is complimentarily step-shaped to the lip of the scoring device and to the overhang portion, such that the second lifting device is configured to be inserted into the hole until the lip contacts the overhang portion, to thereby position the bridge portion at a second predetermined lift distance into the sinus cavity, which is greater than the first predetermined lift distance.

4. The dental implant system of claim 3, wherein the second predetermined lift distance is between about 2 and 4 millimeters.

5. The dental implant system of claim 3, wherein the second predetermined lift distance is about 3 millimeters.

6. The dental implant system of claim 1, wherein the first predetermined lift distance is between about 0.5 and 1.5 millimeters.

7. The dental implant system of claim 1, wherein the first predetermined lift distance is about 1 millimeter.

8. The dental implant system of claim 1, further comprising:

a membrane separation elevator including:

a separation elevator shaft; and a separation elevator head that is substantially flat and attached at a distal end of the separation elevator shaft;

wherein the separation elevator shaft is configured to be inserted through the hole, into the sinus cavity; and wherein the separation elevator head is configured to be inserted between a sinus membrane and the sinus cavity wall, to cause separation therebetween.

9. The dental implant system of claim 1, further comprising:

a boring device configured to bore the hole in the alveolar bone to a predetermined depth, leaving the bridge portion intermediate the hole and the maxillary sinus cavity.

10. A dental implant system for use in installing a dental implant in a hole in an alveolar bone of a maxilla, adjacent a sinus cavity having a sinus membrane lining the sinus cavity, the hole being formed with a bridge portion separating the hole from a bottom surface of a sinus cavity wall, the dental implant system comprising:

a scoring device including a circular shaft with a circular scoring structure formed at a top end of the shaft, the scoring structure including a raised scoring edge formed around a circumference of a concavity formed within the scoring structure, wherein the scoring structure has an outer diameter that is less than an outer diameter of the shaft, and wherein the scoring device further includes a radially outwardly extending step-shaped lip formed intermediate the scoring structure and the shaft, and wherein the scoring structure is configured to cut a score for use in separating the bridge portion from the sinus cavity wall to form an overhang portion along a side of the hole, adjacent an upper opening of the hole;

a first lifting device including a circular shaft, a circular lifting portion of a first height positioned adjacent a top end of the shaft, and a radially outwardly extending lip formed intermediate the shaft and the lifting portion, wherein an outer diameter of the shaft of the first lifting device is substantially the same as the outer diameter of the shaft of the scoring device, and an outer diameter of the lifting portion is substantially the same as the outer diameter of the scoring structure of the scoring device, and wherein the lip of the first lifting device is complimentarily step-shaped to the lip of the scoring device and to the overhang portion, such that the first lifting device is configured to be inserted into the hole until the lip contacts the overhang portion, to thereby position the bridge portion at a first predetermined lift distance into the sinus cavity;

a membrane separation elevator including a separation elevator shaft and a separation elevator head that is substantially flat and attached at a distal end of the separation elevator shaft, wherein the separation elevator shaft is configured to be inserted through the hole, into the sinus cavity, and wherein the separation elevator head is configured to be inserted between a sinus membrane and the sinus cavity wall, to cause separation therebetween; and a second lifting device including a circular shaft, a circular lifting portion of a second height that is greater than the first height the circular lifting portion being positioned adjacent a top end of the shaft, the second lifting device further including a radially outwardly extending lip formed the shaft of the second lifting device is substantially the same as the outer diameter of the shaft of the scoring device, and an outer diameter of the lifting portion of the second lifting device is substantially the same as the outer diameter of the scoring structure of the scoring device, and wherein the lip of the second lifting device is complimentarily step-shaped to the lip of the scoring device and to the overhang portion, such that the second lifting device is configured to be inserted into the hole until the lip contacts the overhang portion, to thereby position the bridge portion at a second predetermined lift distance into the sinus cavity, which is greater than the first predetermined lift distance.

* * * * *